United States Patent [19]
Jernberg

[11] Patent Number: 6,123,957
[45] Date of Patent: *Sep. 26, 2000

[54] DELIVERY OF AGENTS AND METHOD FOR REGENERATION OF PERIODONTAL TISSUES

[76] Inventor: Gary R. Jernberg, 2283 Northridge Dr., North Mankato, Minn. 56003

[ * ] Notice: This patent issued on a continued prosecution application filed under 37 CFR 1.53(d), and is subject to the twenty year patent term provisions of 35 U.S.C. 154(a)(2).

[21] Appl. No.: 08/895,137

[22] Filed: Jul. 16, 1997

[51] Int. Cl.[7] .............................. A61F 13/00; A61C 5/00; A61K 38/18; A61K 31/70

[52] U.S. Cl. .......................... 424/435; 424/434; 433/215; 433/229; 514/12; 514/21; 514/22; 514/23; 514/62

[58] Field of Search ...................... 433/215, 229; 424/426, 434, 435; 514/2, 12, 21, 22, 23, 62

[56] References Cited

U.S. PATENT DOCUMENTS

| | | | |
|---|---|---|---|
| 2,174,796 | 10/1939 | Luzzi | 32/34 |
| 2,835,628 | 5/1958 | Saffir | 167/84 |
| 3,618,604 | 11/1971 | Ness | 128/260 |
| 3,811,444 | 5/1974 | Heller et al. | 128/260 |
| 3,887,699 | 6/1975 | Yolles | 424/19 |
| 3,960,150 | 6/1976 | Hussain et al. | 128/260 |
| 3,972,995 | 8/1976 | Tsuk et al. | 424/28 |
| 3,991,766 | 11/1976 | Schmitt et al. | 128/335.5 |
| 4,001,388 | 1/1977 | Shell | 424/14 |
| 4,121,940 | 10/1978 | Michel et al. | 106/35 |
| 4,141,973 | 2/1979 | Balazs | 424/180 |
| 4,175,326 | 11/1979 | Goodson | 433/80 |
| 4,226,848 | 10/1980 | Nagai et al. | 424/19 |
| 4,249,531 | 2/1981 | Heller et al. | 128/260 |
| 4,250,163 | 2/1981 | Nagai et al. | 424/14 |
| 4,276,880 | 7/1981 | Malmin | 128/221 |
| 4,292,299 | 9/1981 | Suzuki et al. | 424/16 |
| 4,321,038 | 3/1982 | Porteous | 433/136 |
| 4,321,711 | 3/1982 | Mano | 3/1.4 |
| 4,524,065 | 6/1985 | Pinnell | 424/94 |
| 4,534,349 | 8/1985 | Barrows | 128/334 |
| 4,536,387 | 8/1985 | Sakamoto et al. | 424/14 |
| 4,568,536 | 2/1986 | Kronenthal et al. | 424/22 |
| 4,568,538 | 2/1986 | Boden et al. | 424/49 |
| 4,636,524 | 1/1987 | Balazs et al. | 514/781 |
| 4,645,668 | 2/1987 | Pinnell | 424/94 |
| 4,650,665 | 3/1987 | Kronenthal et al. | 424/435 |
| 4,657,548 | 4/1987 | Nichols | 623/10 |
| 4,669,474 | 6/1987 | Barrows | 128/334 |
| 4,685,883 | 8/1987 | Jernberg | 433/215 |
| 4,701,320 | 10/1987 | Hasegawa et al. | 424/54 |
| 4,703,108 | 10/1987 | Silver et al. | 530/356 |
| 4,711,780 | 12/1987 | Fahim | 424/145 |
| 4,713,243 | 12/1987 | Schiraldi et al. | 424/151 |
| 4,736,024 | 4/1988 | Della Valle et al. | 536/55.3 |
| 4,745,161 | 5/1988 | Saudek et al. | 525/420 |
| 4,764,377 | 8/1988 | Goodson | 424/435 |
| 4,776,890 | 10/1988 | Chu | 106/161 |
| 4,780,320 | 10/1988 | Baker | 424/493 |
| 4,789,662 | 12/1988 | Thoms-Leurquin et al. | 514/21 |
| 4,789,663 | 12/1988 | Wallace et al. | 514/21 |
| 4,795,467 | 1/1989 | Piez et al. | 623/16 |
| 4,816,339 | 3/1989 | Tu et al. | 428/421 |
| 4,828,563 | 5/1989 | Müller-Lierheim | 623/16 |
| 4,837,285 | 6/1989 | Berg et al. | 530/356 |
| 4,839,175 | 6/1989 | Guo et al. | 424/450 |
| 4,840,941 | 6/1989 | Ueno et al. | 514/59 |
| 4,841,962 | 6/1989 | Berg et al. | 128/156 |
| 4,851,521 | 7/1989 | Della Valle et al. | 536/55.1 |
| 4,886,787 | 12/1989 | De Belder et al. | 514/57 |
| 4,892,516 | 1/1990 | Härle | 604/57 |
| 4,892,733 | 1/1990 | Bichon et al. | 424/422 |
| 4,954,298 | 9/1990 | Yamamoto et al. | 264/4.6 |
| 4,961,707 | 10/1990 | Magnusson et al. | 433/215 |
| 4,989,601 | 2/1991 | Marchosky et al. | 128/399 |
| 5,032,445 | 7/1991 | Scantlebury et al. | 428/158 |
| 5,059,123 | 10/1991 | Jernberg | 433/214 |
| 5,129,824 | 7/1992 | Keller | 433/215 |
| 5,197,882 | 3/1993 | Jernberg | 433/215 |
| 5,290,271 | 3/1994 | Jernberg | 604/891.1 |

FOREIGN PATENT DOCUMENTS

| | | |
|---|---|---|
| 0 216 453 | 4/1897 | European Pat. Off. . |
| 0 224 987 | 6/1987 | European Pat. Off. . |
| 0 270 317 | 6/1988 | European Pat. Off. . |
| 0 293 090 | 11/1988 | European Pat. Off. . |
| 0 295 092 | 12/1988 | European Pat. Off. . |
| 0 406 665 A1 | 1/1991 | European Pat. Off. . |
| 2 033 232 | 5/1980 | United Kingdom . |
| 2 103 927 | 3/1983 | United Kingdom . |
| 2 146 525 | 4/1985 | United Kingdom . |
| WO 86/00517 | 1/1986 | WIPO . |
| WO 87/06129 | 10/1987 | WIPO . |
| WO 87/07898 | 12/1987 | WIPO . |
| WO 91/04058 | 4/1991 | WIPO . |

OTHER PUBLICATIONS

Erkki Ruoslahti' et al, Minireview, *Cell*, vol. 44, 517–518, Feb. 28, 1986.

Addy, M., et al., "Comparison of the immediate effects on the sub–gingival microflora of acrylic strips . . . ", *Journal of Clinical Periodontology* 1984: 11: 379.

Addy, M., et al., "The development and in vitro evaluation of acrylic strips . . . ", *Journal of Periodontology* 1982: 53: 693.

(List continued on next page.)

*Primary Examiner*—William R. A. Jarvis
*Attorney, Agent, or Firm*—Merchant & Gould P.C.

[57] ABSTRACT

The invention relates to a method of treating periodontal disease and related disorders to regenerate lost tissues, which includes the steps of: combining at least one tissue regenerative agent with at least one cellular recognition agent to form a therapeutic treatment composition and applying the therapeutic treatment composition to a periodontal treatment site. The cellular recognition agent increases the periodontal tissue regeneration at the periodontal treatment site relative to the therapeutic treatment composition lacking the cellular recognition agent. The invention also includes the therapeutic composition.

12 Claims, 2 Drawing Sheets

OTHER PUBLICATIONS

Addy, M., et al., "Simple bacteriological methods to assess changes in subgingival microflora . . . ", *Journal of Clinical Periodontology* 1984: 11: 467.

Ahlfeld, S., et al., "Anterior cruciate reconstruction in the chronically unstable knee . . . ", *American Journal of Sports Medicine* 1987: 15(4): 326–330.

Amis, A., et al., "Anterior cruciate ligament replacement", *J. Bone Joint Surg (Br)* 1988: 70–B(4): 628–634.

Aukhil, I., et al., "An experimental study of new attachment procedure in beagle dogs", *Journal of Periodontal Research* 1983: 18: 643–654.

Baker, P., et al., "Tetracycline and its derivatives strongly bind to and are released from the tooth surface in active form", *Journal of Periodontology* 1983: 580–585 (first page only).

Becker, W., et al., "Root isolation for new attachment procedures", *J. Periodontol.* 1987: 58(12): 819–826.

Caffesse, R., et al., "New attachment achieved by guided tissue regeneration in beagle dogs", *J. Periodontol.* 1988: 589–594.

Caton, J., et al., "Histometric evaluation of periodontol surgery—II. Connective tissue attachment levels after four regenerative procedures", *Journal of Clinical Periodontology* 1980: 7: 224–231.

Chung, K., et al., "Clinical evaluation of a biodegradable collagen membrane in guided tissue regeneration", *J. Periodontol.* 1990: 61(12): 732–736.

Dacey, L., et al., "Intraarterial 9–β–methyl carbacyclin improves canine polytetrafluoroethylene graft patency", *Journal of Vascular Surgery* 1988: 8(1): 21–27.

Gager, A., et al., "Treatment of periodontal defects with an absorbable membrane . . . ", *J. Periodontol* 1991: 62(4): 276–283.

Genco, "Antibiotics in the treatment of human periodontal diseases", *J. Periodontol.* 1981: 52(9): 545–558.

Golub, L. et al., "Tetracyclines inhibit tissue collagenases", *Journal of Periodontology* Supp. 1985: 93–97 (first page only).

Goodson, J., et al., "Clinical responses following periodontal treatment by local drug delivery", *Journal of Periodontology* Supp. 1985: 81.

Goodson, J., et al., "Monolithic tetracycline–containing fibers for controlled delivery to periodontal pockets", *J. Periodontol.* 1983: 54(10): 575–579.

Goodson, J., et al., "Periodontal disease treatment by local drug delivery", *Journal of Periodontology* 1985: 56: 265.

Goodson, J., et al., "Periodontal therapy by local delivery of tetracycline", *Journal of Clinical Periodontology* 1979: 6: 83–92.

Gottlow, J., et al., "New attachment formation as the result of controlled tissue regeneration", *Journal of Clinical Periodontology* 1984: 11: 494–503.

Gottlow, J., et al., "New attachment formation in the human periodontium by guided tissue regeneration" (name of publication unknown), 1985: 604–615.

Horbach, N., et al., "Instruments & methods—A suburethral sling procedure with polytetrafluoroethylene for the treatment of genuine stress incontinence in patients with low urethral closure pressure", *Obstetrics & Gynecology* 1988: 71(4): 648–652.

Hughes, S., "Treatment of infected implants, antibiotic acrylic composites", *Orthopaedic Review* 1987: 16(4): 233/59–235/61.

Isidor, F., et al., "New attachment–reattachment following reconstructive periodontal surgery", *Journal of Clinical Periodontology* 1985: 12: 728–735.

Isidor, F., et al., "The significance of coronal growth of periodontal ligament tissue for new attachment formation" (name of publication unknown), 1985:145–150.

Karring, T., et al., "Healing following implantation of periodontitis affected roots into bone tissue", *Journal of Clinical Periodontology* 1980: 7: 96–105.

Kornman, K., et al., "The effect of long–term low–dose tetracycline therapy on the subgingival microflora in refractory adult periodontitis", *Journal of Periodontology* 1982: 53: 604.

Lindhe, J., et al., "Local tetracycline delivery using hollow fiber devices in periodontal therapy", *Journal of Clinical Periodontology* 1979: 6: 141–149.

Mabry, T., et al., "Freeze–dried bone allografts combined with tetracycline in the treatment of juvenile periodontitis", *Journal of Periodontology* 1985: 56: 74.

Magnusson, I., et al, "Connective tissue attachment formation following exclusion of gingival connective tissue and epithelium during healing", *Journal of Periodontal Research* 1985: 20: 201–208.

Melcher, A., "On the repair potential of periodontal tissues", *Journal of Periodontology* 1976: 47(5): 256–260.

Minabe, M., et al., "Application of a local drug delivery system to periodontal therapy: I. Development of collagen preparations with immobilized tetracycline", *J. Periodontol.* 1989: 60(2): 113–117.

Newman, H., et al., "Slow release metronidazole and a simplified mechanical oral hygiene regimen in the control of chronic periodontitis", *Journal of Clinical Periodontology* 1984: 11: 576.

Nordestgaard, A., "Optimal duration of antiplatelet therapy after implantation of a small–diameter polytetrafluoroethylene arterial prosthesis", *Current Surgery* Nov.–Dec. 1987: 490–493.

Nyman, S., et al., "New attachment following surgical treatment of human periodontal disease", *Journal of Clinical Periodontology* 1982: 9: 290–296.

Nyman, S., et al., "New attachment formation by guided tissue regeneration" 1986 (source of article unknown), 252–254.

Nyman, S., et al., "The regenerative potential of the periodontal ligament", *Journal of Clinical Periodontology* 1982: 9: 257–265.

Pitaru, S., et al., "Heparan sulfate and fibronectin improve the capacity of collagen barriers to prevent apical migration of the junctional epithelium", *J. Periodontol.* Oct. 1991: 62(10): 598–601.

Pontoriero, R., et al., "Guided tissue regeneration in degree II furcation–involved mandibular molars—A clinical study", (source of article unknown) 1987: 247–254.

Pontoriero, R., et al., "Guided tissue regeneration in the treatment of furcation defects in man" (source of article unknown) 1987: 618–620.

"Proceedings from the state of the art workshop on surgical therapy for Periodontitis", sponsored by National Institute of Dental Research, National Institutes of Health, May 13–14, 1981; pp. 475–501.

Raber, P., "Gum disease alleviated by pellets", *Dentistry Today,* Jun. 1986: 5(5) (one page).

Reigel, M., et al., "Early experience with a new collagen––impregnated aortic graft", *The American Surgeon* Mar. 1988: 54: 134–136.

Roth, J., et al., "Synovial reaction associated with disruption of polypropylene braid–augmented intraarticular anterior cruciate ligament reconstruction—A case report", *The American Journal of Sports Medicine* 1988: 16(3): 301–305.

Schreuders, P., et al., "Normal wound healing compared to healing within porous Dacron implants", *Journal of Biomedical Materials Research* 1988: 22: 121–135.

Sevastjanova, N., et al., "Biochemical characterization of connective tissue reaction to synthetic polymer implants", *Biomaterials* 1987: 8: 242–247.

Shoenfeld, N., et al., "A new primate model for the study of intravenous thrombotic potential and its modification", *Journal of Vascular Surgery* Jul. 1988: 8(1): 49–54.

Smith, T., et al., "Thrombosed polytetrafluoroethylene hemodialysis fistulas: Salvage with combined thrombectomy and angioplasty", *Radiology* 1989: 171: 507–508.

Stabholz, A., et al., "Clinical and microbiological effects of sustained release chlorhexidine in periodontal pockets", *J. Clin. Periodontol.* 1986: 13: 783–788 (first page only).

van der Lei, B., et al., "Expanded polytetrafluoroethylene patch for the repair of large abdominal wall defects", *Br. J. Surg.* Aug. 1989: 76: 803–805.

Wan Yusof, W., et al., "Subgingival metronidazole in dialysis tubing and subgingival chlorhexidine irrigation in the control of chronic inflammatory periodontal disease", *Journal of Clinical Periodontology* 1984: 11: 166–175 (first page only).

Yeung, F., et al., "Subgingival metronidazole in acrylic resin vs. chlorhexidine irrigation in the control of chronic periodontitis", *Journal of Periodontology* 1983: 54: 651–657 (first page only).

Young, E., et al., "Infections in prosthetic devices", *Surgical Clinics of North America* Feb. 1988: 68(1): 167–180.

Brochure: "Gore–Tex™ Periodontal Material", © 1987 W. L. Gore & Associates, Inc., Flagstaff, AZ (7 pages).

Brochure: "VICRYL® Periodontal Mesh (Polyglactin 910)—A synthetic bioabsorbable barrier for periodontal tissue regeneration procedures—Efficacy Studies", ©1990 Johnson & Johnson Consumer Products Inc., Skillman, New Jersey (9 pages).

Brochure: "VICRYL® Periodontal Mesh (Polyglactin 910)—A synthetic, bioabsorbable barrier for periodontal tissue regeneration procedures—Use Manual", © 1990 Johnson & Johnson Consumer Products Inc., Skillman, New Jersey (12 pages).

Brochure: "Gore–Tex® periodontal material in extra–large configurations", ©1988, W. L. Gore & Associates, Inc., Flagstaff, AZ (2 pages).

Brochure: Gore–Tex® periodontal material performance review, ©1988, W. L. Gore & Associates, Inc., Flagstaff, AZ (8 pages).

Brochure: "Your Choice—Gore–Tex® periodontal material for guided tissue regeneration", ©1987, W. L. Gore & Associates, Inc. (6 pages).

"The International Journal of Periodontics & Restorative Dentistry", 1988: 4: 9–32.

DELIVERY OF AGENTS AND METHOD FOR REGENERATION OF PERIODONTAL TISSUES

TECHNICAL FIELD OF THE INVENTION

The present invention relates to compositions and methods of treating periodontal disease and related disorders utilizing agents to enhance periodontal tissue regeneration.

BACKGROUND OF THE INVENTION

Periodontal diseases are a major dental affliction to mankind. Periodontitis, inflammation and progressive loss of ligament and alveolar (socket) bone support to tooth, is caused by bacteria which colonize tooth surfaces and occupy the gingival crevice area. Extraction of impacted third molars in close proximity to erupted second molars can also leave damage or loss of support to the second molars.

Regeneration of lost periodontal tissues is a goal of periodontal therapy but is usually not achieved to a maximum or desired level. This is due to the complexities and difficulties associated with periodontal wound healing: Infected, degraded or effete tissue elements must be digested and eliminated and the healing site must be kept free of pathogens. Populations of progenitor cells with the capacity to undergo extensive cell division must be adjacent to the wound site. The dividing cells must respond to soluble and matrix factors by appropriate numbers of mitoses and differentiation steps to become specialized, synthetic cells. The progenitor and specialized cells must migrate to the appropriate site for matrix synthesis. At the wound site, self-renewing cell populations must be established to repopulate the tissue for longterm maintenance. The nascent matrix and attachment components must be stably integrated and undergo remodeling to restore tissue architecture and function. Finally, the repopulating cells must be able to synthesize appropriate growth, differentiating and signaling factors to restore dynamic tissue homeostasis. See C. A. G. McCulloch, *Periodontal Regeneration*, pp. 16–25, Periodontology 2000, Volume 1 Munksgaard, Copenhagen, 1993. The progenitor cells must differentiate into cementoblasts (to form new peripheral hard root surface covering or cementum), fibroblasts (to form new periodontal ligament) and osteoblasts (to form new supporting alveolar bone). Moreover, the periodontal ligament must integrate appropriately with surface covering or cementum), fibroblasts (to form new periodontal ligament) and osteoblasts (to form new supporting alveolar bone). Moreover, the periodontal ligament must integrate appropriately with both the new cementum and bone to form a complete and truly functional periodontal attachment apparatus. Further, this regeneration of periodontal tissues should yield maximum regeneration of lost periodontal tissues along the avascular root surface. These criteria are very difficult to achieve and are rarely met clinically. Therefore, efficacy and predictability are major problems in periodontal regeneration.

A large array of peptide growth and migration factors have been identified. A group of naturally occurring molecules known as polypeptide growth factors in conjunction with certain matrix proteins are key regulators of the biological events of migration, attachment and proliferation of cells. Of these, fibroblast growth factor (FGF), platelet-derived growth factor (PDGF), insulin-like growth factor (IGF), transforming growth factor (TGF) and epidermal growth factor (EGF) appear to have an important role in periodontal wound healing. See R. G. Caffesse and C. R. Quinones, *Periodontal Regeneration*, pp. 69–79, Periodontology 2000, Volume 1 Munksgaard, Copenhagen, 1993.

During the initial phases of periodontal wound healing, a fibrin clot is formed at the site of the periodontal procedure (e.g., periodontal flap surgery). This constitutes the first step toward formation of the extracellular matrix. Various cells involved with the healing process actively contribute to the formation and organization of this matrix. Besides serving as a substrate, it contains a number of secreted biologically active factors acting as chemoattractants and biomodulators that trigger a variety of responses from the cellular components of the healing site. See S. Amar and K. M. Chung, *Clinical Implications Cellular Biologic Advances in Periodontal Regeneration*, p.p. 128–140, Current Opinion in Periodontology, Current Science, Philadelphia, 1994. Outcomes, however, usually result in incomplete periodontal regeneration due to the aforementioned difficulties in periodontal regeneration coronally (toward the crown of the tooth) along the root surface and competitive epithelial downgrowth along the internal aspect of the soft tissue wound (e.g., the repositioned periodontal surgery flap).

Periodontal guided tissue regeneration membranes have been developed and used, upon surgical placement, to separate the tooth root, periodontal ligament and bone from the gingival soft tissues (periodontal or surgical flap) to blockade epithelial downgrowth along the soft tissue wound. This allows for independent regeneration of lost periodontal tissues along the root surfaces. Again, outcomes are equivocal in both efficacy and predictability as this technology does not address optimization of the regenerative system. It acts solely as a mechanical blockade to segregate healing tissue compartments.

Applicant's U.S. Pat. Nos. 5,059,123 and 5,197,882 deal with the sustained, controlled release of chemotherapeutic agents from microshapes incorporated into periodontal barriers to effect a more favorable periodontal regeneration by the use of these agents to enhance cellular healing events and/or diminish negative healing factors (e.g., infection). Applicant's previous method does not address a specific application to the root surface to optimize periodontal regeneration events along this surface.

Applicant's U.S. Pat. No. 4,685,883 deals with local delivery of chemotherapeutic agents to the periodontal defect for sustained, controlled release by either incorporation into microshapes introduced into the defect or by adhesively positioning a biodegradable matrix, including a chemotherapeutic agent thereon, subgingivally on the root surface within the periodontal pocket. Applicant's previous method here does not specifically address the important cofactor of enhancing cell migration along the root surface with maximum coronal periodontal tissue regeneration.

Application of agents against the root surface, by surgical placement, to augment healing has been studied. IGF-1 and PDGF, in combination with methylcellulose gel, were used by syringe application during periodontal surgery in beagle dogs to enhance periodontal regeneration. See S. E. Lynch, R. C. Williams and A. M. Polson, et al, *A Combination of Platelet-Derived and Insulin-Like Growth Factors Enhances Periodontal Regeneration*. J Clin Periodontal 16:545–548, 1989. The coordinated regrowth of the periodontium seen in this study may be due to the ability of PDGF and/or IGF-1 to attract all the cell types necessary for the formation of all of the periodontal tissues with stimulation of proliferation as these cells migrate into the wound site. Although the periodontal regeneration was significant relative to controls, it was limited. The duration of the PDGF/IGF-1 in the region was relatively short-lived and may have contributed to the lack of a more complete healing along the root surface. Further, no specific mechanism of enhancing cell migration along the root surface was addressed.

Study of the cellular recognition of several proteins which interact with cell surfaces led to the observation that three amino acids—an arginine-glycine-aspartic acid (RGD) tripeptide—are crucial for their interaction with cell surface receptors. See E. Ruoslahti and M. D. Pierschbacher, *Arg-Gly-Asp: A Versatile Cell Recognition Signal*, Cell 44:517–518 (1986). Many adhesive proteins present in extracellular matrices and in blood contain RGD as their cell recognition site. These include fibronectin, vitronectin, osteopontin, collagens, thrombospondin, fibrinogen and von Willebrand factor. The RGD sequences of each of the adhesive proteins are recognized by at least one member of a family of structurally related receptors, cell integrins, which can bind to the RGD sequence of adhesion proteins. Some of these receptors bind to the RGD sequence of a single adhesion protein only, whereas others recognize groups of them. Together, the adhesion proteins and their receptors constitute a versatile recognition system providing cells with anchorage, traction for migration, and signals for polarity, position, differentiation and possibly growth. Sao E. Ruoslahti and M. D. Pierschbacher, *New Perspectives in Cell Adhesion: RGD and Integrins*, Science 238: 491–497 (1987).

The present invention solves problems in the regeneration of lost periodontal tissues by optimizing the availability of tissue regenerative agents along the root surface in the site of desired periodontal regeneration and by enhancing cellular migration, differentiation, proliferation and maturation of the regenerative periodontal tissues along the root surface for maximal regeneration.

SUMMARY OF THE INVENTION

The present invention relates to the compositions and methods providing for the delivery of agents to localized periodontal sites for regeneration of lost periodontal tissues and/or for enhanced cellular migration, differentiation and proliferation to favorably effect accelerated, more complete, and/or maximal healing and periodontal tissue regeneration along the root surface of tooth.

In one embodiment of the present invention, a method of periodontal regeneration is provided whereby at least one tissue regenerative agent is combined with at least one cellular recognition agent and is applied to a periodontal treatment site. The cellular recognition agent augments, potentiates, and facilitates the action of the tissue regenerative agent, for example, by providing retention of the tissue regenerative agent at the desired periodontal site, or by providing cellular recognition for cell migration, or by enhancing periodontal tissue regeneration.

In another embodiment of the present invention, a therapeutic treatment composition is provided, composed of at least one tissue regenerative agent and at least one cellular recognition agent. This composition results in retention of the tissue regenerative agent at the desired periodontal site and/or cellular recognition for cell migration and/or enhanced periodontal tissue regeneration.

In yet another embodiment of the present invention, the cellular recognition agent(s) providing for retention of the tissue regenerative agents(s) at the desired periodontal site and/or cellular recognition for cell migration and/or enhanced periodontal tissue regeneration also provides for sustained and/or controlled release of the tissue regenerative agent(s) at the intended periodontal treatment site.

In still another embodiment of the present invention, the tissue regenerative agent(s) is microencapsulated and then combined with the cellular recognition agent(s) providing for retention of the tissue regenerative agent(s) at the desired periodontal site and/or cellular recognition for cell migration and/or enhanced periodontal tissue regeneration with sustained, controlled release of the tissue regenerative agent (s).

In all of the embodiments of the compositions and methods of the present invention, the agent(s) providing for cellular recognition increases the periodontal regeneration of the tissue regenerative agent(s) relative to compositions and methods lacking the cellular recognition agent(s).

These and various other advantages and features of novelty which characterize this invention are pointed out with particularity in the claims annexed hereto and forming a part hereof. However, for a better understanding of the invention, its advantages, and objectives attained by its use, reference should be made to the drawings which form a further part hereof, and to the accompanying descriptive matter, in which there is illustrated and described preferred embodiments of the invention.

BRIEF DESCRIPTION OF THE DRAWINGS

In the drawings, in which like reference numerals and letters indicate corresponding parts throughout the several views.

DETAILED DESCRIPTION OF THE INVENTION

Figure 1A:
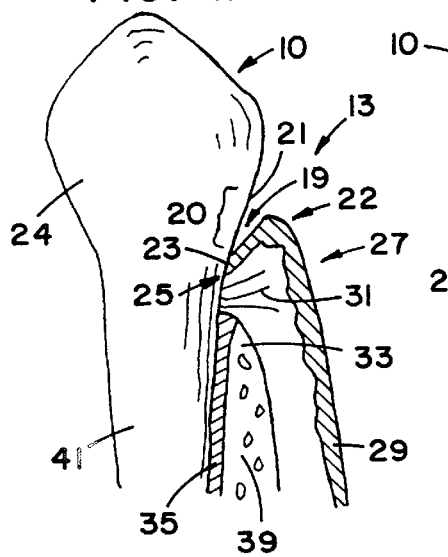
FIGS. 1A through 1C are diagrammatic views illustrating the human periodontal anatomy, including an illustration of the healthy human periodontium in FIG. 1A, an illustration of the effects of gingivitis in FIG. 1B, and an illustration of the effects of periodontitis in FIG. 1C.
Figure 1B:
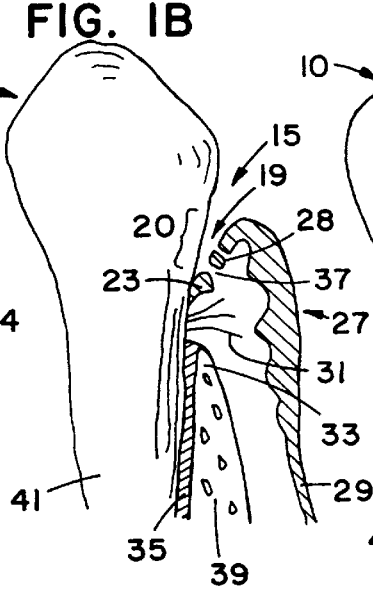
Figure 1C:
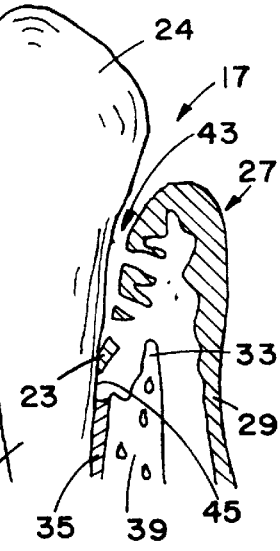
Figure 2:
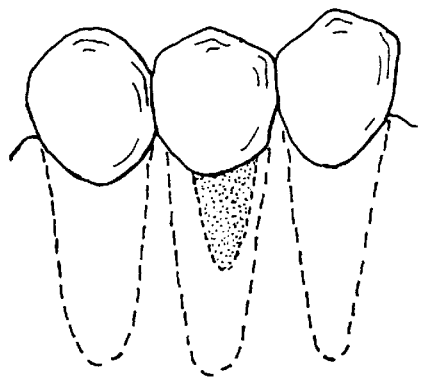
FIG. 2 in a partial diagrammatic view illustrating the placement into a periodontal pocket lesion, between the tooth and gingival tissue, of a gel, paste or viscid liquid.

Referring now to FIGS. 1A through 1C, wherein there in diagrammatically illustrated a human periodontal anatomy 10, progressing from a healthy human periodontium 13 illustrated in FIG. 1A to a periodontium afflicted with periodontitis 17 illustrated in FIG. 1C.

Specifically, FIG. 1A illustrates a healthy human periodontium 13. Between the gingival margin 21 and the free gingiva 22 in the healthy gingival sulcus or crevice 19. The depth 20 of the gingival sulcus or crevice 19, from the gingival margin 21 to the attachment of the junctional epithelium 23, is approximately 1–3 millimeters. The junctional epithelium attaches to the tooth 24 at the cemento-enamel junction (CW) 25. The gingival tissues 27, including the epithelium 29 and gingival fibers 31, are healthy and without inflammation. The alveolar bone crest 33 and periodontal ligament 35 are undamaged.

FIG. 1B illustrates the human periodontium 10 afflicted with gingivitis 15. The gingival tissues 27 show signs of inflammation and crevicular ulceration 37, resulting in white cell infiltration into the gingival sulcus or crevice 19. Furthermore, the ulcerations 37 in the crevicular epithelium 28 result in bleeding upon provocation, such as through brushing and/or flossing of the tooth and gums.

FIG. 1C illustrates the human periodontium afflicted with periodontitis 17. The gingival tissues 27 are inflamed. The alveolar bone crest 33 and periodontal ligament 35 have broken down due to both bacterial and host defense factors.

The breakdown of the attachment of the alveolar bone 39 and periodontal ligament 35 to the tooth root 41 has resulted in the formation of a periodontal pocket lesion 43. In addition, apical proliferation of the junctional epithelium 23 is noted along the root surface 45. A chronic white cell infiltrate in the periodontal pocket lesion 43 is persistent. If left untreated, the continual loss of alveolar bone tissue 39 would result in the loss of the tooth 24.

Accordingly, the present invention provides methods and compositions for the treatment and periodontal regeneration of lost periodontal tissues from periodontal disease and related disorders. Specifically, in a first aspect, the present invention provides a method of treating periodontal disease and regenerating lost periodontal tissues comprising combining at least one tissue regenerative agent with at least one cellular recognition agent to form a therapeutic treatment composition and applying the therapeutic treatment composition to a periodontal treatment site, wherein the cellular recognition agent increases periodontal regeneration at the localized periodontal treatment site relative to a therapeutic treatment composition lacking in the cellular recognition agent.

In a second aspect, the present invention provides a method of treating periodontal disease and regenerating lost periodontal tissues comprising combining at least one tissue regenerative agent with at least one cellular recognition agent to form a therapeutic treatment composition and applying the therapeutic treatment composition into periodontal defects and along root surfaces during periodontal surgical procedures.

In a third aspect, the present invention provides the cellular recognition agent(s) acting an a "caging" molecule to effect sustained, controlled release of the tissue regenerative agent(s).

In a fourth aspect, the present invention provides the tissue regenerative agent(s) which can be microencapsulated and combined with the cellular recognition agent(s) to effect sustained, controlled release of the tissue regenerative agent(s).

A variety of tissue regenerative agents can be utilized in the compositions and methods of the present invention. For example, polypeptide growth factors singularly or in combinations could be used to regenerate lost periodontal tissues. Tetracyclines or modified derivatives could be used as a fibroblast chemoattractant. Dexamethasone has shown potential for strong mitogenesis in synergy with PDGF.

A variety of modified extracellular matrix biomolecules can act as a cellular recognition agent to help facilitate periodontal tissue regeneration by, for example, helping to regulate cell proliferation, migration and/or differentiation. Collagen, glycosaminoglycans (e.g., hyaluronic acid, heparin sulfate, chondroitin sulfate), proteoglycans (e.g., versican, biglycan) and substrate adhesion molecules (e.g., fibronectin, vitronectin, laminin), for example, can be utilized in this capacity.

It will be appreciated that the therapeutic treatment compositions according to the composition and methods of the present invention can occur in any form. Specifically, the therapeutic treatment compositions can occur in a solid form, a semi solid form (e.g., gel or paste), a liquid form or combinations thereof. For example, in certain applications the therapeutic treatment compositions can be comprised of a tissue regenerative agent(s) formed as solid microparticulates interspersed in a gel comprising the cellular recognition agent(s). In other applications, the tissue regenerative agent(s) can be mixed with the cellular recognition agent(s) to form a paste, gel or viscid liquid. In yet other applications the tissue regenerative agent(s) can be mixed with the cellular recognition agent(s) to effect molecular "caging" of some of the tissue regenerative agent(s) within the molecular net or coiling of the cellular recognition agent(s).

Figure 3:
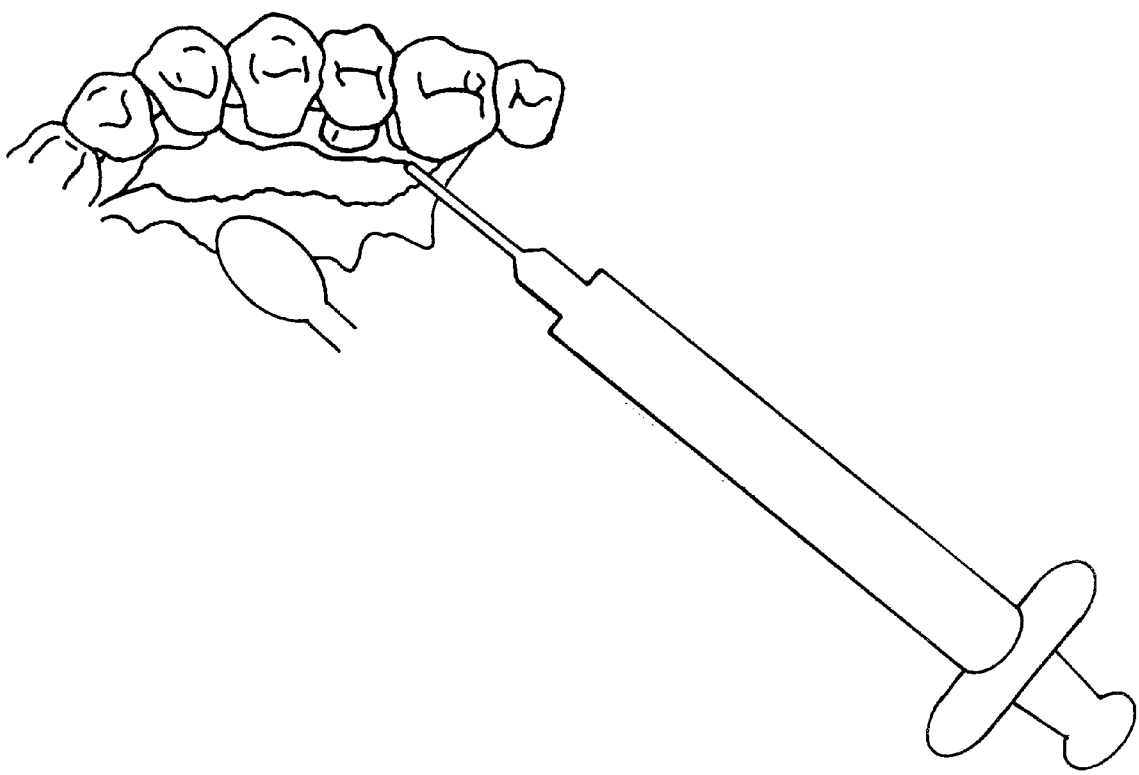
FIG. 3 is a partial diagrammatic view of placement of a gel, paste or viscid liquid into the periodontal defects during periodontal surgery.

As illustrated in FIG. 3, in a particularly preferred embodiment of the present invention, the therapeutic composition is incorporated into a gel and applied by syringe to the periodontal defects where regeneration is desired during periodontal surgery. The therapeutic composition can also be applied by other methods known to those of skill in the art for applying agents to periodontal tissue, such as using a carrying instrument.

The tissue regenerative agent is supplied to the site of periodontal disease in an amount effective to facilitate or accelerate periodontal tissue regeneration. Typically, the therapeutic composition contains an effective amount of tissue regenerative agent in the range of about 0.00002 mg/ml to about 100 mg/ml, preferably about 0.0005 mg/ml to about 10 mg/ml, preferably about 0.001 mg/ml to about 3 mg/ml. For example, when the tissue regenerating agent is a bone morphogenetic protein, such as BMP2 or BMP3, the composition contains an effective amount of bone morphogenetic protein in the range of about 0.1 mg/ml to about 100 mg/ml, preferably about 0.2 mg/ml to about 10 mg/ml, preferably about 0.3 mg/ml. For example, when the tissue regenerating agent is an insulin-like growth factor, such as IGF-1, a platelet derived growth factor, such as PDGF, or a combination of such growth factors, the composition contains an effective amount of growth factor in the range of about 0.00002 mg/ml to about 5 mg/ml, preferably about 0.00005 mg/ml to about 2 mg/ml, preferably about 0.0001 mg/ml.

The cellular recognition agent is supplied to the site of periodontal disease in an amount effective to augment, potentiate, or facilitate the activity of the tissue regenerative agent. Although not limiting to the present invention, it is believed that the cell recognition agent acts by facilitating cell migration and/or retaining the tissue regenerative agent at the site of periodontal disease. Typically, the therapeutic composition contains an effective amount of cellular recognition agent in the range of about 0.02 wt-% to about 30 wt-%, preferably about 0.1 wt-% to about 10 wt-%, preferably about 1 wt-% to about 5 wt-%. For example, when the cellular recognition agent is hyaluronic acid, an ester of hyaluronic acid, a salt of hyaluronic acid, a crosslinked gel of hyaluronic acid, or a derivative of hyaluronic acid, the therapeutic composition contains an effective amount of cellular recognition agent in the range of about 0.1 wt-% to about 10 wt-%, preferably about 2.5 wt-%.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

What is claimed is:

1. A method of treating periodontal disease and related disorders to regenerate lost tissues comprising:
 combining a tissue regenerative agent with a cellular recognition agent to form a therapeutic treatment composition in the form of a semi-solid, a paste, a liquid, a gel, or a combination thereof; and applying the therapeutic treatment composition to a periodontal treatment site by inserting the therapeutic treatment composition into a periodontal defect at the periodontal treatment site solely via a carrying instrument or a syringe, wherein the cellular recognition agent increases the periodontal tissue regeneration at the periodontal treatment site relative to the therapeutic treatment composition lacking the cellular recognition agent.

2. A method according to claim 1, wherein the tissue regenerative agent comprises a polypeptide growth factor, a developmental growth factor, a bone morphogenetic protein, a fibroblast chemoattractant, a steroid, or a combination thereof.

3. A method according to claim 2, wherein the polypeptide growth factor comprises a platelet-derived growth factor, a fibroblast growth factor, a transforming growth factor, an insulin-like growth factor, or a combination thereof.

4. A method according to claim 1, wherein the cellular recognition agent comprises a collagen, a glycosaminoglycan, a proteoglycan, a non-collagen protein of the extracellular matrix, or a combination thereof.

5. A method according to claim 4, wherein the glycosaminoglycan comprises a hyaluronic acid, a chondroitin sulfate, an heparin, an heparin sulfate, a keratan sulfate, or a combination thereof.

6. A method according to claim 1, wherein combining comprises chemical modification of the cellular recognition agent incorporating the tripeptide arginine-glycine-aspartic acid (RGD).

7. A method according to claim 1, wherein applying comprises inserting the therapeutic treatment composition into a periodontal defect during periodontal surgery via instrument or syringe.

8. A method according to claim 1, wherein combining comprises selecting microspheres sized between approximately 10 to 700 microns in diameter.

9. A method according to claim 8, wherein combining comprises encapsulating the tissue regenerative agent into the microspheres.

10. A method according to claim 8, wherein encapsulating comprises selecting a microsphere having a time release value for substantially continuous release of the therapeutic treatment composition over a predetermined period of time.

11. A method according to claim 8, wherein combining comprises mixing the tissue regenerative agent with a polymer comprising the microspheres.

12. A method according to claim 1, wherein combining comprises mixing the tissue regenerative agent with the cellular recognition agent, encompassing or caging the tissue regenerative agent molecularly, and affecting sustained, controlled release of the tissue regenerative agent.

* * * * *